United States Patent [19]
Clagett

[11] Patent Number: 4,746,631
[45] Date of Patent: May 24, 1988

[54] IMMUNOASSAY METHOD, DEVICE, AND TEST KIT

[75] Inventor: James A. Clagett, Seattle, Wash.

[73] Assignee: Ultra Diagnostics Corporation, Seattle, Wash.

[21] Appl. No.: 732,445

[22] Filed: May 9, 1985

[51] Int. Cl.$^4$ .................. G01N 33/53; G01N 33/543
[52] U.S. Cl. ..................... 436/518; 436/514; 436/807; 436/808; 436/809; 422/61
[58] Field of Search ............ 422/56, 57, 58, 61; 435/7; 436/514, 518, 531, 807, 808, 809, 810, 819, 820

[56] References Cited

U.S. PATENT DOCUMENTS

| | | | |
|---|---|---|---|
| 3,715,192 | 2/1973 | Wenz | 422/56 |
| 4,017,597 | 4/1977 | Reynolds | 436/810 |
| 4,146,365 | 3/1979 | Kay et al. | 422/57 |
| 4,225,575 | 10/1980 | Piasio et al. | 436/531 |
| 4,272,478 | 6/1981 | Vihko | 422/57 |
| 4,289,747 | 9/1981 | Chu . | |
| 4,330,299 | 5/1982 | Cerami . | |
| 4,425,438 | 1/1984 | Bauman et al. . | |
| 4,434,236 | 2/1984 | Freytag . | |
| 4,436,094 | 3/1984 | Cerami . | |
| 4,446,232 | 5/1984 | Liotta | 435/7 |

*Primary Examiner*—Sidney Marantz
*Assistant Examiner*—Janelle Graeter
*Attorney, Agent, or Firm*—Christensen, O'Connor, Johnson & Kindness

[57] ABSTRACT

An immunoassay device includes one or more reaction chambers. Each reaction chamber is adapted to receive and retain a volume of test fluid in fluid communication with nonoverlapping first and second reaction surfaces. To the first reaction surface is immobilized analyte binding partner that is in turn saturated with analyte conjugate: analyte component conjugated to one or more components, termed ligand/marker, that serve ligand and marker functions as described herein. The analyte conjugate has a higher disassociation constant with reference to the immobilized analyte binding partner than does the analyte to be assayed. To the second reaction surface is immobilized ligand/marker binding partner.

A test fluid sample is introduced into the reaction chamber and retained therein to permit two reactions to occur. In a first reaction between analyte and analyte binding partner at the first reaction reaction surface, analyte proportionately displaces analyte conjugate into the test fluid sample. In a second reaction the displaced analyte conjugate becomes sequestered at the second reaction surface by bonding with immobilized ligand-/marker binding partner. Thereafter the marker activity of sequestered analyte analog is measured, the measured activity being a function of the analyte concentration that is referable to standards and controls.

A test kit includes the immunoassay device in combination with comparative test results.

48 Claims, 3 Drawing Sheets

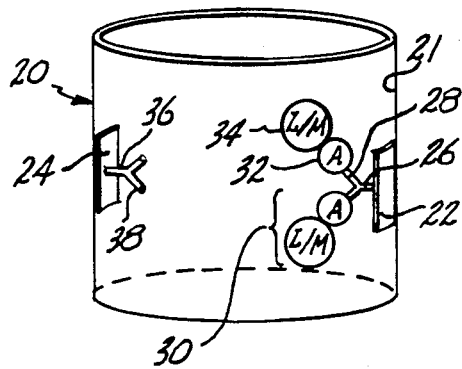
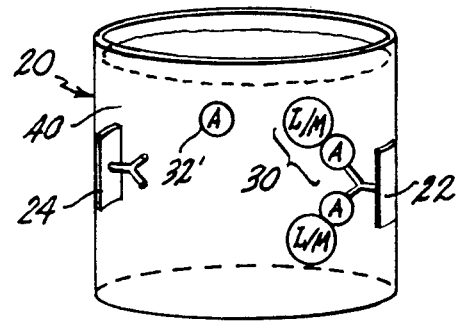
Fig.1.
Fig.2.
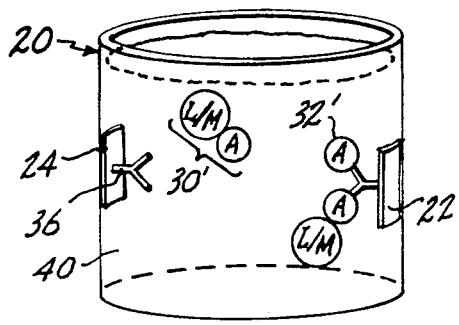
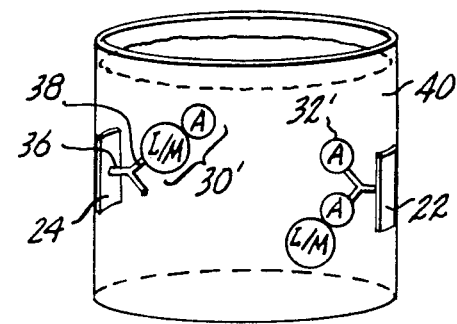
Fig.3.
Fig.4.

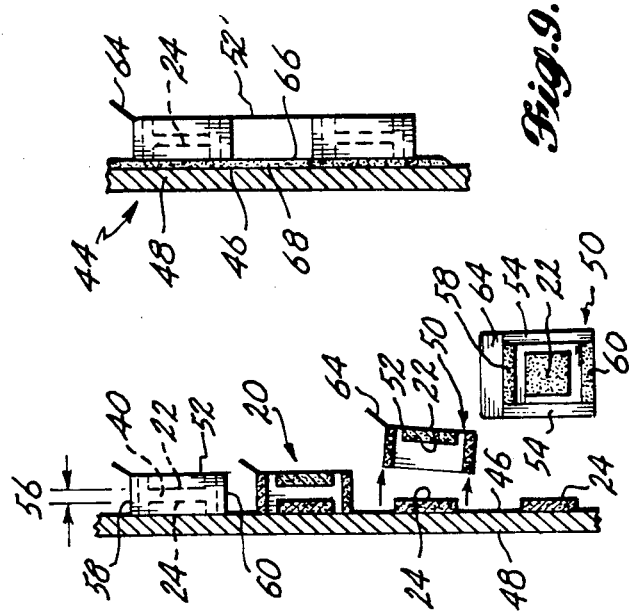
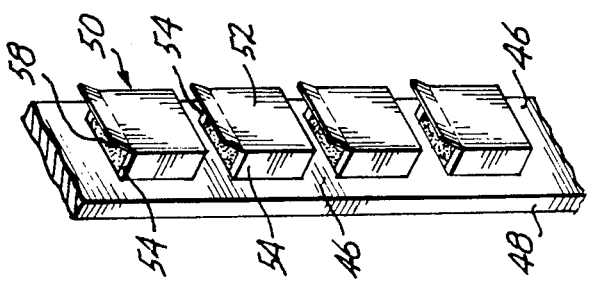
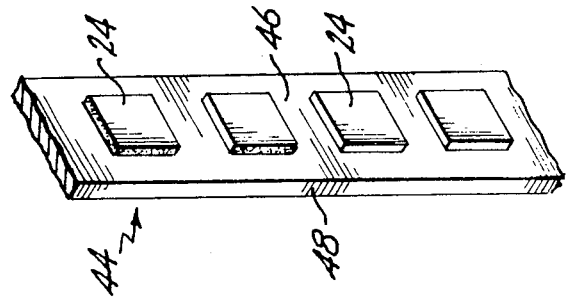
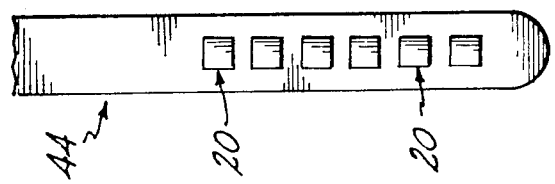

IMMUNOASSAY METHOD, DEVICE, AND TEST KIT

TECHNICAL FIELD

This invention relates to immunoassays and more particularly to heterogeneous immunoassays in which analyte in test fluid displaces a labeled moiety from an insoluble support.

BACKGROUND OF THE INVENTION

Various heterogeneous immunoassays for the detection and quantification of analyte molecules in a liquid sample are known, and several employ the displacement of a labeled moiety from an insoluble support.

In this regard, U.S. Pat. No. 4,330,299 is of interest for disclosing a method for measuring the level of glucose in animal body fluids which comprises contacting a portion of a given body fluid with a glucose indicator comprising a reversible complex of a carbohydrate component, a binding macromolecular component, and an indicator element bound to one of the components. The sample of body fluid is maintained in contact with the glucose indicator for a period of time sufficient to permit the glucose present to displace the carbohydrate component in the reversible complex, whereby the indicator element is released to signify the presence of glucose. This assay suffers from the disadvantage that its applicability is restricted to glucose and other sugars.

U.S. Pat. No. 4,425,438 discloses an assay method and flowthrough test device in which test substance may displace an analytical reagent, which can be the test substance chemical labeled with a detectable group and with a group capable of binding specifically to an analytical absorbant, from a primary absorbant. A column is provided with two zones, a primary absorbant zone and an analytical absorbant zone, through which the assay fluid, admixed with a predetermined quantity of analytical reagent, is sequentially passed. Any analytical reagent not bound by the primary absorbant substance becomes bound to the analytical absorbant substance. The presence of analytical reagent bound to the analytical absorbant substance is then determined. A principal disadvantage of this assay is that the specific amounts of primary absorbant in the primary absorbant zone and of analytical reagent mixed with the assay fluid must be carefully balanced to insure that no analytical reagent will pass through the beads if no test substance is present, and, at the same time, at least some analytical reagent will pass through the beads if test substance is present in the assay fluid.

U.S. Pat. No. 4,434,236 discloses an immunoassay wherein labeled antibody having greater affinity for analyte in the fluid sample than for immobilized analyte-analogue is displaced from the solid phase. A principal disadvantage of this assay is that the fluid sample containing displaced labeled antibody must be analyzed by means, such as by spectrophotometer or fluorometer, that do not lend themselves to home or field use. Another disadvantage is that labeled divalent antibodies cannot be accurately employed in this assay.

While perhaps advantageous for certain applications, none of these prior art devices and methods provide a single-step, self-contained test device that can be conveniently used by a nontechnical user for on-site testing. It would also be advantageous to provide an integrated device that can be conveniently manufactured and used to detect and quantify the presence of several different analytes in a single application.

BRIEF DESCRIPTION OF THE DRAWINGS

FIG. 1 is a schematic diagram of an immunoassay reaction chamber of this invention, wherein an analyte binding partner having analyte-specific binding sites that are saturated with analyte conjugate (analyte component conjugated with ligand/marker component) is immobilized on a first reaction surface, and wherein a ligand/marker binding partner is immobilized on a second reaction surface;

FIG. 2 is identical fo FIG. 1 except that a test fluid sample containing analyte has been introduced into the reaction chamber;

FIG. 3 is identical to FIG. 2 except that analyte in the retained test fluid sample has displaced analyte analog from analyte-specific binding site at the first reaction surface, and the displaced analyte analog has diffused or been mixed into the test fluid sample;

FIG. 4 is identical to FIG. 3 except that the displaced analyte conjugate has contacted and bound to ligand/marker binding partner at the second reaction surface;

FIG. 5 is a plan view of a dipstick having a plurality of reaction chambers of this invention;

FIG. 6 is an oblique view showing a spaced series of second reaction surfaces on the test surface of an insoluble support;

FIG. 7 is a view similar to FIG. 6 except that a series of reaction chamber housings are cooperatively mounted on the test surface to span and cover the second reaction surfaces;

FIG. 8 is a section of the device of FIG. 7 showing juxtaposed first and second reaction surfaces within the reaction chambers and also indicating the detachable mounting of the reaction chamber housing and wicks;

FIG. 9 is a view similar to FIG. 8 but showing an embodiment wherein substrate is releasably sequestered on the insoluble support;

SUMMARY OF THE INVENTION

Figure 10:
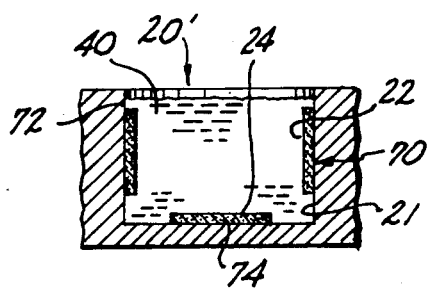
FIG. 10 is a section of a reaction chamber having the form of a modified microtiter well.

This invention provides a single step, self-contained test device for detecting and quantifying analyte molecules in a fluid sample. No auxiliary reactants other than a test fluid need be supplied or added to this test device, which can be conveniently used by the lay public in the home or field without auxiliary instrumentation. Moreover, an integrated test device is provided that can be conveniently custom-manufactured and used to detect and quantify several different analytes in a simple application.

The disclosed test device includes one or more reaction chambers of this invention. Each reaction chamber is adapted to receive and retain a volume of test fluid in fluid communication with nonoverlapping first and second reaction surfaces. To the first reaction surface is immobilized analyte binding partner that is in turn saturated with analyte conjugate: analyte component conjugated to one or more components, collectively termed ligand /marker, that serve ligand and marker functions as described herein. The analyte conjugate has a higher disassociation constant with reference to the immobilized analyte binding partner than does the analyte to be assayed. To the second reaction surface is immobilized ligand/marker binding partner.

In the practice of this invention, a test fluid sample is introduced into the disclosed reaction chamber and retained therein to permit two reactions to occur. In a first reaction between analyte and analyte binding partner at the first reaction surface, analyte proportionately displaces analyte conjugate into the test fluid sample. In a second reaction the displaced analyte conjugate becomes sequestered at the second reaction surface by bonding with immobilized ligand/marker binding partner. Thereafter the marker activity of sequestered analyte analog is measured, the measured activity being a function of the analyte concentration that is referable to standards and controls.

Also provided is a test kit that includes the disclosed test device in combination with comparative test results that associate sequestered ligand/marker activity with specific concentrations of analyte in test fluid.

DESCRIPTION OF THE PREFERRED EMBODIMENTS

Referring to FIG. 1, a device is provided for detecting the presence and concentration of an analyte in a test fluid. A reaction chamber 20 designed to receive and retain a volume of test fluid is provided with containment walls 21 and with first and second reaction surfaces 22, 24. The reaction surfaces 22, 24 are disposed in nonoverlapping and preferably noncontiguous arrangement within the reaction chamber 20 such that the first reaction surface 22 is in fluid communication with the second reaction surface 24 after a predetermined volume of test fluid is introduced into the reaction chamber 20 (see FIG. 2).

To the first reaction surface 22 a multiplicity, on the order of millions, of analyte binding partners 26 are immobilized such that in the preferred embodiment analyte-specific binding sites 28 on the immobilized analyte binding partners 26 are potentially available in log excess over the expected concentration of analyte in the predetermined volume of test fluid. The available analyte-specific binding sites 28 on the immobilized analyte binding partners 26 are saturated with analyte conjugate 30, which in the simplest embodiment consists of an analyte molecule 32 conjugated with a ligand/marker molecule 34. The analyte binding partner 26 is selected such that its analyte-specific binding sites 28 have a higher affinity for free analyte in the test fluid than for the particular analyte conjugate 30; that is, under the assay conditions the analyte conjugate 30 has a higher disassociation constant with reference to the analyte binding partner 26 than does the analyte in the test fluid.

To the second reaction surface 24 a multiplicity of ligand/marker binding partners 36 are immobilized such that ligand/marker-specific binding sites 38 on the immobilized ligand/marker binding partners 36 are available in log excess over the expected concentration of analyte in the predetermined volume of test fluid.

Referring now to FIGS. 1, 2, 3 and 4, a method is provided for detecting the presence and concentration of an analyte in a test fluid. A reaction chamber 20 is provided in accordance with the foregoing discussion referring to FIG. 1.

Referring to FIG. 2, a volume of test fluid 40 containing (or suspected of containing) analyte molecules 32' is introduced into the reaction chamber 20 so that at least parts of the first and second reaction surfaces 22, 24 are covered by the test fluid sample 40. For stoichiometrical quantification of analyte 32' concentration a predetermined volume of test fluid 40 should be introduced into the reaction chamber 20 and, furthermore, the first and second reaction surfaces 22, 24 should be thereby completely submersed.

Referring to FIGS. 2, 3 and 4, the test fluid sample 40 is retained within the reaction chamber 20 for an incubation period that can be on the order of thirty minutes, depending upon ambient temperature. During the incubation period two reactions occur within the fluid-filled reaction chamber 20. At the first reaction surface 22 analyte 32' will displace analyte conjugate 30 from analyte binding partner 26, which displacement reaction proceeds by virtue of the higher affinity of the analyte-specific binding sites 28 for analyte 32' than for analyte conjugate 30. Any displaced analyte conjugate 30' diffuses through the test fluid sample 40, which diffusion process can be enhanced by stirring the test fluid sample 40, and upon contacting the second reaction surface 24 the displaced analyte conjugate 30' binds to ligand/marker binding partner 36 via a bond between ligand/marker component 34 and ligand marker-specific binding site 38.

Subsequent to the incubation period the marker activity of the ligand/marker 34 on the second reaction surface 24 is measured, that activity being a function of the concentration of analyte 32' in the test fluid and referable to standards and controls.

In order to simplify this discussion, analyte 32' is considered unless otherwise stated to be an immunogenic molecule such as an antigen or hapten, and analyte binding partner 26 is considered to be an antibody having analyte 32'-specific binding sites 28, as this is the preferred embodiment. However, in the practice of this invention, analyte 32' can be any molecule for which an analyte binding partner 26 exists or can be raised or synthesized. Thus, it is also contemplated that in the practice of this invention analyte 32' can be an antibody and analyte binding partner 26 can be an antigen or hapten, in which case both the analyte and the analyte component of the analyte conjugate would have binding sites (not shown) that are specifically reactive with the immunogenic analyte binding partner immobilized on the first reaction surface 22.

Test fluid sample 40 can be any aqueous source of analyte 32'; for example, physiological fluids such as anti-coagulated blood, plasma, urine, tissue extract, or saliva, in which case the analyte 32' can be any endogenous or exogenous molecule, such as a hormone or a therapeutic or abused drug and their metabolites. Test fluid 40 must be aqueous or largely so, containing only small amounts of organic solvents so that analyte binding partner 26 and analyte conjugate 30 will not spontaneously dissociate in the test fluid sample 40. In this regard the analyte 32' must also be available in aqueous solution for binding with analyte binding partner 26. Thus, to detect serum protein-bound hormones such as cortisol, detergent can be added to the test fluid sample 40 in order to release the hormone analyte 32' from the protein carrier and thereby make it fully available to an analyte binding partner 26 having cortisol-specific binding sites 28. Such detergents and other agents, where applicable, can be placed on the containment walls 21, e.g., by evaporation or impregnation, prior to packaging the reaction chamber 20 in order to maintain the simplicity of the disclosed assay protocol.

Reaction chamber 20 is configured to receive a test fluid sample 40 and retain the same (including any displaced analyte conjugate 30′) throughout the incubation period. For stoichiometrical determinations of analyte 32′ concentration, reaction chambers 20 of uniform volume should be provided. The containment walls 21 (other than the reaction surfaces 22, 24) that contain the test fluid sample 40 within the reaction chamber 20 can be made of any insoluble material, e.g., plastic, nylon, polypropylene, polyvinylchloride, or polyvinylcarbonate, that does not react with either analyte 32′ or displaced analyte conjugate 30′. Reaction chambers 20 of this invention can take the form of test tubes, microtiter wells, or self-contained dipsticks as described below.

First reaction surface 22 and second reaction surface 24 are each composed of a binding substrate, which can be a molecular film, having the capacity to bind reactants via covalent or strong ionic bonds such that analyte binding partner 26 and ligand/marker binding partner 36 can be irreversibly immobilized on the first and second reaction surfaces 22, 24, respectively. Suitable binding substrates for this purpose include derivatized celluloses such as nitrocellulose, bromacetyl cellulose, cyanogen bromide activated cellulose, and also derivatized nylon, derivatized plastics, and other activated polymers.

Analyte binding partner 26 is preferably a monoclonal antibody having at least one binding site 28 that is specifically reactive to analyte 32′ and to analyte component 32 and that in addition has a higher affinity for analyte 32′ than for analyte conjugate 30. Analyte binding partner 26 can be a divalent antibody or an antibody polymer (or polymerized Fab fragments) having a plurality of analyte-specific binding sites 28. However, it is contemplated that steric hindrance between the available analyte-specific binding sites 28 should be minimized for stoichiometrical quantification purposes, in which case a monovalent antibody or Fab fragment is the preferred analyte binding partner 26.

Analyte binding partner 26 can be covalently bonded to first reaction surface 22 by conventional techniques; for example, by conventional reactions involving carbonyl groups, carboxyl groups, the ε-amino acid groups of lysine, or the SH groups of cysteine, by strong ionic interactions, and by specific interaction with protein A. A multiplicity of analyte binding partners 26 are bound to the first reaction surface 22 so that analyte-specific binding sites 28 are thereafter available for binding with analyte 32′ or analyte component 32 in log excess over the expected concentration of analyte 32′ in the test fluid sample 40. To this end, through the use of heterobifunctional chemical compounds and through other chemical reactions known in the art, analyte binding partner 26 can be immobilized on first reaction surface 22 in specific orientation in order to make analyte-specific binding site 28 available to analyte component 32 of analyte conjugate 30 and to analyte 32′ in test fluid sample 40. Moreover, the accessibility with regard to steric hindrance of available analyte-specific binding sites 28 can be enhanced by selectively distributing analyte binding partner 26 on the first reaction surface 22. Optimal density of particular analyte binding partners 26 can be achieved by selective chemical activation of the first reaction surface 22 or by using immunoaffinity membranes 22 that are commercially available, e.g., BIODYNE immunoaffinity membrane (PALL, Biodyne Division, Glen Cove, N.Y.).

Analyte conjugate 30 is a conjugated molecule: analyte component 32 bonded to ligand/marker 34. Ligand/marker 34 is a molecule or molecules or conjugated molecule that perform(s) two function: Ligand/marker 34 acts as a ligand to provide specific binding of displaced analyte conjugate 30′ to ligand/marker binding partner 36 at the second reaction surface 24. Ligand/marker 34 also acts as a marker that can be detected by conventional techniques such as enzymatic color development. For certain applications ligand/marker 34 may also perform a third function by acting as a macromolecular carrier in order to ensure the retention of displaced analyte conjugate 30′ within the reaction chamber 20.

The aforesaid functions can be performed by ligand/markers 34 that consist of either a single molecule, or a conjugate of a ligand component bonded to a marker component, or a conjugate of a carrier component bonded to both a ligand component and a marker component. Alternatively, a ligand component and marker component can be individually conjugated at separate sites to the analyte component 32 to make analyte conjugate 30. For example, the fluorescent phycobiliprotein molecule can act as a convenient ligand/marker 34 that advantageously combines the aforesaid ligand, marker, and macromolecular carrier functions in a single molecule. As another example, ligand/marker 34 can be horseradish peroxidase (HPO) conjugated with a ligand such as biotin, in which case the HPO, having a molecular weight of about 40,000, functions both as a marker component and as a macromolecular carrier.

Suitable ligand components include: biotin, bovine serum albumin (BSA), synthetic peptides, phycobiliproteins, and β-galactosidase, all of which have readily available ligand/marker binding partners 36 as described below.

Suitable marker components include: enzymes such as HPO, β-galactosidase, and alkaline phosphatase; chromophores or organic dyes such as phthalocyanine; fluorophores such as fluorescein, phycobiliprotein, or rhodamine; coenzymes such as FAD; chemiluminescent materials such as luciferin; enzyme inhibitors such as phosphonates; and radionuclides. If the marker component is an enzyme useful for colorimetric assay, the reaction product should be insoluble so that the marker activity will be sequestered at the second reaction surface 24. Peroxidase substrates fulfill this requirement. Chemiluminescence, due to the extraordinary sensitivity of the enhanced signal, is preferred for detecting analyte 32′ such as hormones at very low concentations.

Suitable macromolecular carrier components include BSA and other proteins of greater than, e.g., 10,000 molecular weight. Smaller synthetic peptides can also be employed as carrier components to focus the analyte component 32 and the ligand/marker component(s) 34 in specific orientation on the analyte conjugate 30.

In embodiments in which analyte 32′ is an immunogenic molecule, the analyte component 32 of the analyte conjugate 30 can have the same molecular structure as the analyte 32′ to be assayed or can be a metabolic derivative or a synthesized or raised analog thereof. For example, analyte component 32 can be an anti-idiotype antibody to analyte-specific binding site 28. In embodiment wherein analyte 32′ is an antibody, the analyte component 32 can be the same or a different antibody. In all embodiments the analyte component 32 must specifically bind to analyte binding partner 26 and, furthermore, analyte component 32 when conjugated to ligand/marker 34 must have a higher dissociation constant than analyte 32' with reference to analyte binding partner 26.

Monoclonal antibodies can be raised using standard techniques of in vivo or in vitro immunizations. Selection of hybridoma clones producing antibodies with the requisite affinities can be performed by equilibrium dialysis or by determining of relative dissociation constants through a modification of the Farr technique, both as described in Chapters 15 and 16, *Handbook of Experimental Immunology; Vol. 1: Immunochemistry*, Weir (ed.), Blackwell Scientific Publications, G.B., 1973. Fab fragments of monoclonal antibodies can be prepared as described in *J. Immunol.* 131:2895-2902, 1983. Heterobifunctional compounds are disclosed in *Biochem. J.* 173:723-737,1978.

For optimal stoichiometry as many ligand components as possible should be substituted onto analyte conjugate 30 while maintaining the activity of the marker component; also, analyte conjugates 30 should each bear a uniform number of marker components.

To make analyte conjugate 30, ligand/marker 34 can be conjugated to analyte component 32 using strong ionic or covalent bonding, by diazotization, by water soluble carbodiimides, by utilizing available carboxyl groups and amino groups, and by heterobifunctional compounds and other chemical linkages known in the art.

The available analyte-specific binding sites 28 on the first reaction surface 22 are saturated with analyte analog 30 in a separate preparative manufacturing step by incubation for at least one hour at room temperature, followed by removal of excess, unbound analyte conjugate 30 by washing with physiologic salt solution.

Ligand/marker binding partner 36 can be a monoclonal or polyclonal antibody having specific affinity for ligand/marker 34 component (but not for analyte 32 component) of analyte conjugate 30. For example, if BSA serves as the ligand component in ligand/marker 34, then anti-BSA can serve as the ligand/marker binding partner 36. As another example, if biotin serves as the ligand component in ligand/marker 34, then ligand/marker binding partner 36 can be insolubilized avidin. Other representative but nonlimiting examples of ligand/marker binding partners 36 include second partners of activated heterobifunctional substituted ligand/markers 34. Ligand/marker binding partner 36 is irreversibly immobilized on second reaction surface 24 as described above so that ligand marker-specific binding sites 38 are available for binding to ligand/marker 34 in log excess of the expected concentration of analyte 32' (and, proportionally, of displaced analyte conjugate 30') in test fluid sample 40.

Referring now to FIGS. 5 through 9, an improved dipstick 44 can be provided with one or more reaction chambers 20 of this invention.

Referring to FIGS. 6 through 8, in a representative embodiment a plurality of second reaction surfaces 24 are disposed in spaced array along a test surface 46 of an insoluble support 48. Each second reaction surface 24 is covered by an insoluble, impermeable reaction chamber housing 50 that can have the form of a U-shaped channel with a web 52 and two opposing flanges 54. A first reaction surface 22 is disposed on the web 52 between the flanges 54. The flanges 54 are positioned on and detachably mounted to the test surface 46 so that the housing 50 spans the second reaction surface 24 and juxtaposes the two reaction surfaces 22, 24. The flanges 54 are of a height selected so that a minimum diffusion distance 56, no more than about 1.0 mm and preferably on the order of 0.1 mm, separates the first and second reaction surfaces 22, 24. Upper and lower membranes 58, 60 cooperate with the open ends of the housing 50 and with the adjacent test surface 46 to complete the containment walls of a reaction chamber 20 having a test fluid volume capacity on the order of 10 to 50 $\mu$l. The flanges 54 of housing 50 are detachably mounted on the test surface 46, for example by an insoluble adhesive (not shown) having low shear strength. Membranes 58, 60 are typically made of materials having very low shear strength and so can be cooperatively attached to the web 52, flanges 54, and adjacent test surface 46 by any insoluble cement.

The upper and lower membranes 58, 60 function primarily to facilitate the capillary migration of test fluid into the reaction chamber 20. To this end the membranes 58, 60 can each be an open meshwork of very hydrophilic material such as cellulose that, once the dipstick 44 is immersed in test fluid, acts as a wick to draw a test fluid sample into the reaction chamber 20. For certain applications it may be desirable to exclude macromolecules such as plasma proteins from the reaction chamber 20, in which case the membranes 58, 60 can be made of a hydrophilic meshwork having a molecular size exclusion limit. For example, polysulfone membranes and cellulosic polymers may be used to exclude macromolecules of 10,000 molecular weight or larger, and also to retain within the reaction chamber 20 displaced analyte conjugate of the specified size. In another embodiment the lower membrane 60 can be any of the aforementioned hydrophilic wicks, but the upper membrane 58 can be made of a hydrophobic meshwork or porous membrane that acts as a oneway valve to facilitate release of entrapped air as the reaction chamber 20 fills with test fluid. If avidin is used as ligand/marker binding partner 36, then the outside surfaces of membranes 58, 60 can be loaded with insolubilized avidin in order to remove any biotin intrinsic to the test fluid sample.

A tab 64 can be provided as an integral part of each reaction chamber housing 50, on the side of the web 52 opposite the first reaction surface 22, to facilitate detachment of the housing 50 from the test surface 46. Tab 64 also can be applied to a web 52' that integrates a series of reaction chamber housings (see FIG. 9).

In operation, the dipstick 44 is immersed in a test fluid, such as urine, until the reaction chambers 20 are completely filled with a test fluid sample by capillary migration of test fluid through the upper and/or lower membranes 58, 60. The dipstick 44 is then removed from the test fluid and laid on a flat surface, test surface 46 upward, for the duration of the incubation period. During the incubation period surface tension resulting from the hydrophilic nature of the membrane(s) 58, 60 retains the test fluid sample within the reaction chamber 20. After the incubation period has elapsed the tab 64 is pulled to detach the reaction chamber housing 50 from the test surface 46 and thereby expose the second reaction surface 24 for visual or instrumental determination of sequestered ligand/marker activity.

Referring to FIG. 9, if the marker activity on the second reaction surface 24 is to be measured colorimetrically by employment of an enzyme marker component such as HPR in ligand/marker 34, then the appropriate substrate can be incorporated into the dipstick 44. For example, substrate 68 can be sandwiched between the test surface 46 and an insoluble, frangible membrane 66, such as Mylar, adjacent to the second reaction surface 24 and stored there until the incubation period is over. Then the membrane 66 can be crushed to release substrate 68 onto the second reaction surface 24 for local color development due to reaction with any ligand/enzyme marker bound thereon. Substrate 68 can take the form of substrate-saturated membranes as well. Thus the present invention supplies a self-contained test device 44 to which no auxiliary reactants other than test fluid 40 need be added. Such a test device 44 permits a simple, one-dip assay that has obvious advantages for home and field use.

The test device 44 can be provided in kit form in combination with comparative test reults, e.g., a color chart (not shown), that associate the enzyme marker activity with specific concentrations of analyte in test fluid.

Dipsticks 44 of this invention can be conveniently manufactured as well as conveniently used to simultaneously detect and quantify the presence of different analytes in a test fluid. For example, dipstick 44 can be supplied with a plurality of second reaction surfaces 24 each having the same ligand/marker binding partner, e.g., avidin, immobilized thereon. In contrast, the corresponding first reaction surfaces 22 can bear different analyte binding partners to which different analyte conjugates are reversibly bound. However, if the same ligand/marker, e.g., biotin/HPR, is employed throughout, so that the various analyte conjugates differ only with respect to their analyte components, then the same substrate can be used to develop marker activity on each second reaction surface. Moreover, the user can refer to the same color chart to determine the specific concentrations of the different analytes as functions of the observed marker activities on the various second reaction surfaces.

To optimize stoichiometrical quantification the following conditions should be met: analyte-specific binding sites must significantly exceed the number of analyte molecules in the test fluid sample; the dissociation constant of analyte binding partner with respect to analyte analog must be greater than the dissociation constant with respect to analyte; displaced analyte analog must bind essentially irreversibly to ligand/marker binding partner; the time period for developing marker activity on the second reaction surface must be routinely adjusted to render color intensity, fluorescence intensity, or other detectable parameters in direct relation to the quantity of analyte present in the test fluid sample; and ligand analog displacement from analyte binding partner must be associated with analyte binding only. These conditions are met by the reaction chambers of this invention.

Figure 11:
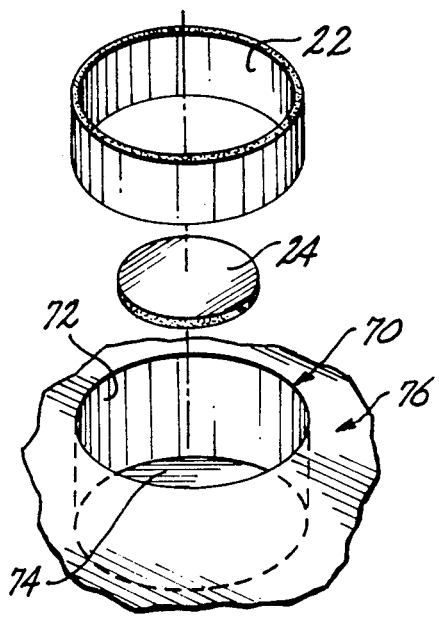
FIG. 11 is an exploded view of FIG. 10.

Referring now to FIGS. 10 and 11, a modified microtiter well 70 having a test fluid volume capacity of 100 to 200 μl can also serve as a reaction chamber 20' of this invention. A first reaction surface 22 can be coaxially disposed on the side 72 of the well 70, and a planar second reaction surface 24 can be disposed to cover all or part of the floor 74 of the well 70. Such a reaction chamber 20' can be conveniently filled with a test fluid sample 40 using an automatic pipette, and following an incubation period any marker activity on the second reaction surface 24 can be conveniently read using, for example, a microfluorometer. A ring of containment wall 21 can be provided at the base of sidewall 72 so that substrate can be added to cover the second reaction surface 24 without contacting the first reaction surface 22. This embodiment 20' is particularly well suited for repetitive laboratory testing by technical personnel using sophisticated instrumentation. For example, a plate 76 can be provided with a plurality of reaction chambers 20' (not shown) for each test fluid to be assayed; some of the reaction chambers 20' can be filled with replicate test fluid samples, and other of the reaction chambers 20' can be filled with control solutions containing known concentrations of the analyte or analytes being assayed.

Figure 12:
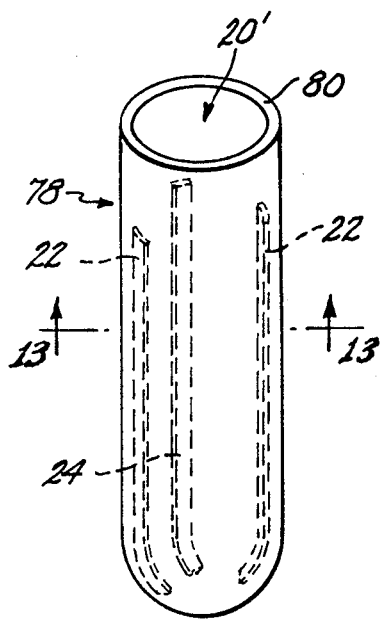
FIG. 12 is a plan view of a reaction chamber having the form of a modified test tube.
Figure 13:
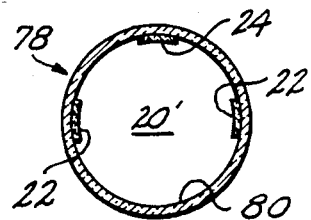
FIG. 13 is a section of FIG. 12.

Referring to FIGS. 12 and 13, in a related embodiment a modified test tube 78 can also serve as a reaction chamber 20' of this invention. For example, first and second reaction surfaces 22, 24 can be disposed in nonoverlapping arrangement on the inner wall 80 of a test tube 78. During the incubation period the test fluid sample (not shown) can be periodically stirred or vortexed in order to effect contacts between analyte and first reaction surface 22 and between analyte-displaced analyte analog and second reaction surface 24. If first and second reaction surfaces 22, 24 are not diametrically opposed on test tube wall 80, then colorimetric or fluorometric marker activity on second reaction surface 24 can be conveniently read by inserting tube 78 into a standard spectrophotometer or fluorometer.

While the present invention has been described in conjunction with a preferred embodiment and illustrative examples, one of ordinary skill after reading the foregoing specification will be able to effect various changes, substitutions of equivalents, and other alterations to the method and device set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A method of detecting an analyte in a test fluid, comprising the steps of:

providing a reaction chamber having nonoverlapping first and second reaction surfaces, the reaction chamber being adapted to receive and retain a predetermined volume of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon;

introducing a volume of the test fluid into the reaction chamber in fluid communication with the first and second reaction surfaces;

retaining the volume of test fluid in the reaction chamber to permit two reactions to occur: a first reaction between analyte and analyte binding partner at the first reaction surface, the analyte thereby proportionally displacing analyte conjugate into the volume of test fluid, and a second reaction between the displaced analyte conjugate and ligand/marker binding partner at the second reaction surface, the displaced analyte conjugate thereby becoming sequestered on the second reaction surface; and, thereafter measuring the activity of sequestered ligand/marker on the second reaction surface, the measured activity being a function of the analyte concentration that is referable to standards and controls.

2. The method of claim 1, wherein the analyte binding partner is an antibody.

3. The method of claim 1, wherein the analyte binding partner is an antigen or hapten.

4. The method of claim 1, wherein the reaction chamber is a test tube.

5. The method of claim 1, wherein the first and second reaction surfaces are noncontiguous.

6. The method of claim 1, wherein the analyte conjugate comprises phthalocyanine.

7. The method of claim 1, wherein the test fluid volume capacity of the reaction chamber is on the order of 10 to 50 µl.

8. The method of claim 7, wherein the first and second reaction surfaces are separated by a diffusion distance of no more than about 1.0 mm.

9. The method of claim 8, wherein the diffusion distance is on the order of 0.1 mm.

10. The method of claim 7, wherein the reaction chamber further comprises wick means for receiving and retaining the volume of test fluid.

11. The method of claim 10, wherein the reaction chamber further comprises valve means for releasing from the reaction chamber air displaced by the received volume of test fluid.

12. The method of claim 7, wherein the reaction chamber is detachably mounted on an insoluble support.

13. The method of claim 12, wherein the second reaction surface is affixed to the insoluble support.

14. The method of claim 13 wherein the insoluble support further comprises means for storing substrate reactive with ligand/marker.

15. A device for detecting an analyte in a test fluid, comprising a reaction chamber having nonoverlapping first and second reaction surfaces, the reaction chamber being adapted to receive and retain a predetermined volume of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon.

16. The device of claim 15, wherein the analyte binding partner is an antibody.

17. The device of claim 15, wherein the analyte binding partner is an antigen or hapten.

18. The device of claim 15, wherein the reaction chamber is a test tube.

19. The device of claim 15, wherein the analyte conjugate comprises phthalocyanine.

20. The device of claim 15, wherein the test fluid volume capacity of the reaction chamber is on the order of 10 to 50 µl.

21. The device of claim 20, wherein the first and second reaction surfaces are separated by a diffusion distance of no more than about 1.0 mm.

22. The device of claim 21, wherein the diffusion distance is on the order of 0.1 mm.

23. The device of claim 20 further comprising wick means for receiving and retaining the volume of test fluid.

24. The device of claim 23 further comprising valve means for releasing from the reaction chamber air displaced by the received volume of test fluid.

25. The device of claim 20, wherein the reaction chamber is detachably mounted on an insoluble support.

26. The device of claim 25, wherein the second reaction surface is affixed to the insoluble support.

27. The device of claim 26 further comprising means for storing substrate reactive with ligand/marker.

28. A method of detecting an analyte in a test fluid, comprising the steps of:

providing a reaction chamber having nonoverlapping first and second reaction surfaces, the reaction chamber being adapted to receive and retain a volume on the order of 100 to 200 µl of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon;

introducing a volume of the test fluid into the reaction chamber in fluid communication with the first and second reaction surfaces;

retaining the volume of test fluid in the reaction chamber to permit two reactions to occur: a first reaction between analyte and analyte binding partner at the first reaction surface, the analyte thereby proportionally displacing analyte conjugate into the volume of test fluid, and a second reaction between the displaced analyte conjugate and ligand/marker binding partner at the second reaction surface, the displaced analyte conjugate thereby becoming sequestered on the second reaction surface; and, thereafter measuring the activity of sequestered ligand/marker on the second reaction surface, the measured activity being a function of the analyte concentration that is referable to standards and controls.

29. The method of claim 28, wherein the reaction chamber is a microtiter well.

30. The method of claim 28, wherein the analyte conjugate comprises phthalocyanine.

31. The method of detecting an analyte in a test fluid, comprising the steps of:

providing a reaction chamber detachably mounted on an insoluble support, the reaction chamber having nonoverlapping first and second reaction surfaces, the reaction chamber being adapted to receive and retain a volume on the order of 10 to 50 µl of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon;

introducing a volume of the test fluid into the reaction chamber in fluid communication with the first and second reaction surfaces;

retaining the volume of test fluid in the reaction chamber to permit two reactions to occur: a first reaction between analyte and analyte binding partner at the first reaction surface, the analyte thereby proportionally displacing analyte conjugate into the volume of test fluid, and a second reaction between the displaced analyte conjugate and ligand/marker binding partner at the second reaction surface, the displaced analyte conjugate thereby becoming sequestered on the second reaction surface; and, thereafter measuring the activity of sequestered ligand/marker on the second reaction surface, the measured activity being a function of the analyte concentration that is referable to standards and controls.

32. The method of claim 31, wherein the analyte conjugate comprises phthalocyanine.

33. The method of claim 31, wherein the reaction chamber is detachably mounted on an insoluble support.

34. The method of claim 33, wherein the first reaction surface is detachably mounted on an insoluble support.

35. The method of claim 33, wherein a plurality of the reaction chambers are detachably mounted on an insoluble support.

36. The method of claim 35, wherein the reaction chambers have identical ligand/marker binding partners but different analyte binding partners.

37. A device for detecting an analyte in a test fluid, comprising a reaction chamber having nonoverlapping first and second reaction surfaces, the reaction chamber being adapted to receive and retain a volume on the order of 100 to 200 $\mu$l of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon.

38. The device of claim 37, wherein the reaction chamber is a microtiter well.

39. The device of claim 37, wherein the analyte conjugate comprises phthalocyanine.

40. The device for detecting an analyte in a test fluid, comprising a reaction chamber detachably mounted on an insoluble support, the reaction chamber having nonoverlapping first and second reaction surfaces, the reaction chamber being adapted to receive and retain a volume on the order of 10 to 50 $\mu$l of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon.

41. The device of claim 40, wherein the second reaction surface is affixed to the insoluble support.

42. The device of claim 40, wherein the first reaction surface is detachably mounted on the insoluble support.

43. The device of claim 40, wherein a plurality of the reaction chambers are detachably mounted on the insoluble support.

44. The device of claim 43, wherein the reaction chambers have identical ligand/marker binding partners but different analyte binding partners.

45. The device of claim 40, wherein the analyte conjugate comprises phthalocyanine.

46. A test kit comprising a device for detecting an analyte in a test fluid, the device comprising a reaction chamber having nonoverlapping first and second reaction surfaces, the reaction chamber being adapted to receive and retain a volume of the test fluid in fluid communication with the first and second reaction surfaces, the first reaction surface having an analyte binding partner immobilized thereon, the analyte binding partner having an analyte conjugate reversibly bound thereto, the analyte conjugate comprising a ligand/marker conjugated to an analyte component, the analyte conjugate having a higher disassociation constant than the analyte with reference to the immobilized analyte binding partner, and the second reaction surface having a ligand/marker binding partner immobilized thereon, in combination with comparative test results that associate ligand/marker activity with specific concentrations of analyte in test fluid.

47. The test kit of claim 46, wherein the comparative test result comprises a color chart.

48. The test kit of claim 46, wherein the analyte conjugate comprises phthalocyanine.

* * * * *

UNITED STATES PATENT AND TRADEMARK OFFICE
CERTIFICATE OF CORRECTION

PATENT NO. : 4,746,631
DATED : May 24, 1988
INVENTOR(S) : Clagett et al.

It is certified that error appears in the above-identified patent and that said Letters Patent is hereby corrected as shown below: On The Title Page:

[75] INVENTOR: "James A. Clagett, Seattle, Wash." should be --James A. Clagett, Everett, Wash., Thomas H. Stanton and Kent E. Opheim, both of Seattle, Wash.--

[57] ABSTRACT, line 10: "disassociation" should be --dissociation--

[57] ABSTRACT, line 18: delete the second occurence of "reaction"

Column 6, line 4: "function" should be --functions--

Column 6, line 63-64: "embodiment" should be --embodiments--

Column 10, line 53: "disassociation" should be --dissociation--

Column 11, line 54: "disassociation" should be --dissociation--

Column 12, line 32: "disassociation" should be --dissociation--

Column 12, line 60: "The" should be --A--

Column 13, line 6: "disassociation" should be --dissociation--

Column 13, line 57: "disassociation" should be --dissociation--

Column 14, line 19: "disassociation" should be --dissociation--

Column 14, line 47: "disassociation" should be --dissociation--

Signed and Sealed this

First Day of November, 1988

*Attest:*

DONALD J. QUIGG

*Attesting Officer*     *Commissioner of Patents and Trademarks*